United States Patent [19]

Bohn et al.

[11] 3,931,399

[45] Jan. 6, 1976

[54] PROCESS FOR ISOLATING A FIBRIN-STABILIZING FACTOR

[75] Inventors: Hans Bohn, Marbach near Marburg an der Lahn; Fritz Emmerich, Marburg an der Lahn, both of Germany

[73] Assignee: Behringwerke Aktiengesellschaft, Marburg an der Lahn, Germany

[22] Filed: Dec. 21, 1973

[21] Appl. No.: 427,252

Related U.S. Application Data

[63] Continuation-in-part of Ser. No. 210,224, Dec. 20, 1971, abandoned.

[30] Foreign Application Priority Data

Dec. 22, 1970 Germany............................ 2063069

[52] U.S. Cl. ................................................ 424/105
[51] Int. Cl.² ......................................... A61K 35/48
[58] Field of Search .................................... 424/105

[56] References Cited
UNITED STATES PATENTS 3,497,492   2/1970   Buck et al. .......................... 424/105

*Primary Examiner*—Stanley J. Friedman
*Attorney, Agent, or Firm*—Curtis, Morris & Safford

[57] ABSTRACT

A process for isolating a fibrin-stabilizing factor, factor XIII, by extracting human placentae with sodium chloride solution; adding diamino-ethoxy-acridine lactate (DEAL); recovering the resultant precipitate and dissolving it in dilute alkali metal chloride solution containing a complexing agent; adding a quaternary ammonium base to the solution to precipitate inactive materials; reprecipitating the active principal from solution with DEAL; again dissolving the precipitate in dilute alkali metal chloride solution containing a complexing agent; reprecipitating the active principal by adding solid ammonium sulfate; forming a paste between the precipitate and a dilute solution of a complexing agent; dialyzing the paste; gel filtering the dialyzed product; precipitating the active principal from the active fractions with ammonium sulfate; dissolving the precipitate in a neutral tris-(hydroxymethyl)-aminomethane hydrochoric acid buffer containing a complexing agent; dialyzing the solution; and precipitating the factor XIII from the remaining solution in the form of euglobulin.

1 Claim, No Drawings

PROCESS FOR ISOLATING A FIBRIN-STABILIZING FACTOR

The present application is a continuation-in-part of U.S. Ser. No. 210,224 filed Dec. 20, 1971 now abandoned.

The present invention relates to a process for isolating a fibrin-stabilizing factor from human placentae.

The fibrin-stabilizing factor, also referred to as factor XIII, plays an important part in blood clotting. If it is missing in the blood, heavy after-bleeding occurs upon injuries and healing of wounds is retarded. The lack of factor XIII may be hereditary or may be the result of diseases, for example cirrhosis of the liver, carcinoma, leukemia, or disseminated intravascular coagulation (DIC). These conditions may become a danger to life, especially for the new-born and for pregnant women, in whom the lack of factor XIII may lead to miscarriage.

These deficiency symptoms may be overcome by substitution, e.g. by the use of blood, plasma, or fibrinogen preparations. However, these substances have to be infused in a large volume, which is undesirable in many cases and is troublesome and time-consuming. Moreover, accompanying proteins and blood-group substances are thus administered to the patient, which may cause incompatibility phenomena. Hence, there is demand for a preparation which has a high fibrin-stabilizing activity and which is, to a large extent, free from accompanying proteins and blood-group substances.

It is known in the art that factor XIII is contained in platelets and in blood plasma and can be isolated therefrom by precipitation with ammonium sulfate, heating, and diethylaminoethyl-cellulose (DEAE cellulose) chromatography. However, the concentration of the fibrin-stabilizing factor in plasma is low and the yield obtained by this known process is, therefore, poor. Further, the heating operation, during which factor XIII is separated from fibrinogen, can only be performed on small batches. Therefore, the process has not been adopted by industry nor gained any importance.

Moreover, plasma as a starting material is too expensive for the industrial preparation of factor XIII. For the same reason, platelets are refused as an industrial source for the production of factor XIII.

It has now been found that the fibrin-stabilizing factor can be isolated in good yield from human placentae.

According to the present invention, frozen human placental tissue is first extracted with dilute sodium chloride solution at a temperature between about 0°C. and about 20°C. The concentration of the sodium chloride solution may be between 0 percent and about 2 percent, preferably about 0.5 percent. As known to those skilled in the art, the amount of extracting solution employed is chosen large enough to bring about an effective extraction, but is kept small enough to avoid the handling of excessive amounts of solution. In general, for the present process, between about 0.5 and 1.5 liters of sodium chloride solution are employed per kilogram of tissue being extracted.

Any solid contaminants are removed from the resulting solution extract by conventional methods, e.g. by centrifugation.

Next, at a temperature of from about 5°C. to about 20°C., a dilute solution of diamino ethoxy acridine lactate (DEAL) is added at a pH from 5.0 to 7.5. The solution, which preferably has a concentration between about 2 percent and 3 percent, is added in an amount such that the DEAL added is from 6 to 10 percent by weight of the protein content of the extract. The protein content of the extract can be determined by the usual analytical methods for quantitative assay of proteins such as by refraction measurements or by the biuret method.

The resulting precipitate is next recovered by centrifugation, may optionally be washed several times with water, and is then dissolved in a dilute alkali metal chloride solution having a concentration between 2 and 7.5%, a pH from 7.0 to 8.0, preferably about 7.5, and containing about 5 percent of a complexing agent, by weight of the alkali metal chloride present. The temperature of the solution is preferably between 5°C. and 20°C. Suitable alkali metal chlorides include sodium chloride and potassium chloride, preferably sodium chloride. As complexing agents, ethylene diamine tetracetic acid (EDTA), and nitrilo-triacetic acid are preferred.

Insoluble substances are then removed from this solution, e.g. by filtration or by centrifugation. If desired, the solution may be diluted further with water to an alkali chloride concentration of 0.5 to 1.0%. Inactive substances which are present in the solution are then precipitated therefrom by adding a quaternary ammonium base to the solution in an amount of from 0.04 percent to 0.08 percent, based on the weight of solution. Suitable quaternary ammonium bases are N-cetyl-pyridinium chloride, alkyl-dimethylbenzyl-ammonium chloride, and dichloro-benzyldimethyl-alkylammonium chloride, of which the first-mentioned is preferred.

Still operating at a temperature between 5°C. and 20°C., and after removal of the precipitated inactive substances, a further precipitate is produced in the resulting filtrate by the addition of further DEAL. Again, a dilute solution having a concentration between 2 percent and 3 percent is preferably employed in an amount sufficient to contribute from 0.1 percent to 0.2 percent of DEAL, based on the volume of the solution.

After separation of the supernatant liquid, this precipitate is dissolved by again adding a dilute solution of an alkali metal chloride as defined above, preferably sodium chloride, at a pH between 7.0 and 8.0, preferably at 7.5, and containing about 5 percent, by weight of the alkali metal chloride, of a complex-forming agent of the type earlier described herein. Any residue remaining in the solution is separated by filtration.

20 – 30 percent, by weight of the solution, preferably about 25 percent, of solid ammonium sulfate is then added to the filtrate with the resultant formation of a precipitate. After a few hours, the precipitate is separated by filtration and made up into a paste with a dilute aqueous solution of a complex-forming agent of the type earlier described herein. The content of complex-forming agent in this solution is about 0.01 M.

This paste is then dialyzed against tris(hydroxymethyl)amino-methane hydrochloric acid buffer having a pH of 7.0 and containing a complex-forming agent of the type earlier described herein together with $NaN_3$. The aqueous buffer solution contains between 0.05 percent and 0.5 percent by weight of tris compound, between 0.1 percent and 1.0 percent by weight of the complex-forming agent, and from 0.01 percent to 0.1 percent of $NaN_3$. Dialysis is continued at a temperature between 0°C. and 10°C. for a period of 12 to 48 hours.

Contaminants in the paste, which forms a solution during dialysis, are removed (e.g. by centrifugation) at a pH of 6.0 after dialysis. The solution is then gelfiltered on a molecular sieve at a neutral pH value.

The fractions so obtained are analyzed using the fibrin-stabilizing factor test described below and those showing an activity of more than 2 units are combined. A precipitate is again separated therefrom by the addition of between 20 percent and 30 percent, by weight of the solution of solid ammonium sulfate. The precipitate is dissolved in neutral tris-EDTA buffer.

This solution is again dialyzed against neutral tris-EDTA buffer. After dialysis for a period of 10 to 20 hours, the pH is adjusted to about 5.0, whereupon the factor XIII precipitates.

For distribution in dosage unit forms, the separated precipitate may be dissolved in physiological sodium chloride solution containing a small amount of one of the aforementioned complex-forming agents at pH 7.0, adjusted with NaOH. A stabilizer, for example human albumin or gelatin which has been degraded by hydrolysis and cross-linked with hexamethylene diisocyanate (available under the registered trademark "Haemaccel"), is then added to the solution. The solution is filtered under sterile conditions, dialyzed against a 0.9% saline solution containing 0.5% glucose at a temperature of 2° to 10°C. for 20 to 50 hours, standardized, and — if desired — lyophilized.

The activity of the fibrin-stabilizing factor is conveniently determined by a dilution test [cf. Thromb diathes. haemorrh. 23, 455 (1970)]. In the test, use is made of the different solubility, in a 1 percent aqueous chloroacetic acid solution, of cross-linked fibrin and fibrin that is not cross-linked because of a lack of fibrin-stabilizing factor. Using thrombin, fibrinogen free of factor XIII, and increasingly-diluted samples of the solution of factor XIII to be determined, fibrin clots are formed having different degrees of cross-linking. These clots are then incubated with a 1 percent solution of chloroacetic acid. The dilution in which the fibrin clot is just still preserved is determined to be the factor-XIII concentration which is just sufficient for cross-linking. In the next higher dilution, the fibrin clot dissolves. Samples having activities of more than 2 units (as defined below) are considered to be active.

Ordinary human mixed plasma serves as a reference substance. The factor-XIII activity contained in 1 ml of human mixed plasma is defined as "one unit". The fibrin-stabilizing activity desired is calculated from the ratio of the limit values for the dilution of mixed plasma and the solution to be tested.

The factor XIII obtained according to the present invention can be used to treat any factor-XIII deficiency symptoms, for example the inherited lack thereof and any haemorrhagic syndromes resulting therefrom, bleeding and disturbances in the healing of wounds, as well as any transitory lack of factor XIII, for example after an operation and a retarded healing of wounds resulting therefrom. A solution containing the factor XIII is injected intravenously, advantageously in an amount corresponding to the factor-XIII activity of 250 ml of fresh human plasma. Where required, up to 4 times this amount may be administered.

The fibrin-stabilizing factor isolated according to the present invention from human placentae does not typically differ from the factor XIII obtained from platelets but it does differ from factor XIII obtained from plasma. The chemical and physico-chemical data are compiled in the following Table I.

TABLE I

| Fibrin-stabilizing factor obtained from | Plasma | Platelets | Placenta |
|---|---|---|---|
| Sedimentation coefficient | 8.4 S | 7.4 S | 7.2 S |
| Molecular weight | 300,000 | 150,000–200,000 | 165,000 |
| Carbohydrate content in % | 4.9 | 1.5 | 1.47 |
| Hexoses | 1.9 | 1.2 | 0.98 |
| Fucose | 0.2 | 0.0 | 0.0 |
| Hexosamine (N-acetyl-) | 1.6 | 0.16 | 0.28 |
| Neuraminic acid (N-acetyl-) | 1.2 | 0.15 | 0.21 |
| Amino acid radicals per 100 amino acids | | | |
| Lysine | 6.3 | 5.7 | 5.1 |
| Histidine | 2.5 | 2.0 | 1.9 |
| Arginine | 5.5 | 6.2 | 6.2 |
| Aspartic acid | 10.4 | 12.2 | 12.2 |
| Threonine | 7.2 | 5.9 | 6.2 |
| Serine | 7.2 | 5.8 | 6.1 |
| Glutamic acid | 12.7 | 10.8 | 11.0 |
| Proline | 5.7 | 4.6 | 4.9 |
| Glycine | 7.9 | 7.1 | 7.0 |
| Alanine | 4.1 | 5.3 | 5.3 |
| Valine | 7.5 | 9.9 | 9.7 |
| Methionine | 2.0 | 2.6 | 2.6 |
| Isoleucine | 4.8 | 5.2 | 5.0 |
| Leucine | 7.3 | 6.8 | 6.7 |
| Tyrosine | 5.0 | 4.2 | 4.4 |
| Phenyl-alanine | 3.9 | 4.5 | 4.6 |
| ½ Cysteine | ? | 1.2 | 1.1 |

A better understanding of the present invention and of its many advantages can be had from the following specific Example, given by way of illustration:

EXAMPLE 1

1500 kg of frozen human placentae (corresponding with about 2400 placentae) having a temperature of about −20°C. were cut into fine pieces and mixed, while stirring, with 1500 liters of a 0.5 percent sodium chloride solution having a temperature of about +20°C. The resulting mixture, the temperature of which is about 0°C., was heated to 10°C. and centrifuged. The fibrin-stabilizing active substance was precipitated at a pH of 6.0 from the tissue-free supernatant solution by the addition of sufficient amount of a 3 percent aqueous solution of DEAL to provide approximately 8 percent of DEAL by weight of the protein content in the solution. The precipitate was isolated by centrifugation.

The centrifuged material was washed by suspension in 900 liters of water at a pH of 7.0 and again centrifuged.

The residue was dissolved at a temperature of 10°C. in 800 liters of a 2.5 percent sodium chloride solution containing 0.125 percent of EDTA, which solution had a pH of 7.5. The solution was stirred and, after four hours, insoluble substances were separated. The supernatant solution was diluted with water to 1500 liters.

30 liters of a 3 percent N-cetyl pyridinium chloride solution were next added to the solution at a pH of 7.0 and a temperature of 15°C., whereby accompanying proteins and mucopolysaccharides were precipitated and eliminated by centrifuging.

75 liters of a 3 percent solution of DEAL were then added to the supernatant solution at a temperature of 15°C., whereupon the fibrin-stabilizing active substance was precipitated.

After removing the supernatant solution by siphoning, the DEAL precipitate was dissolved at a temperature of 10°C. over a period of 1 – 2 hours by stirring with 100 liters of a 5 percent sodium chloride solution containing 250 g of EDTA and having a pH of 7.5. The precipitated DEAL chloride was separated by filtration.

The fibrin-stabilizing factor was next slowly precipitated from the solution by the addition of 25 percent, by weight of the solution, of solid ammonium sulfate at a temperature of 10°C. The precipitate obtained with ammonium sulfate was separated by centrifugation after standing for 3 – 4 hours.

For further purification, 800 g of the ammonium sulfate paste were mixed, while stirring, with a 0.01 molar EDTA solution (pH 7.0) and the paste obtained was dialyzed for 48 hours at 4°C. against a 0.005 molar tris(hydroxymethyl) aminomethane hydrochloric acid buffer (pH 7.0) containing 0.005 mol of EDTA per liter of buffer and 0.05 percent of sodium azide.

Thereafter, the pH of the resulting solution was adjusted to 6.0 with 2% acetic acid. The resulting precipitate was centrifuged and discarded.

The pH of the supernatant solution was adjusted to 7.0 with 0.2 M NaOH solution and the solution was fractionated at a temperature of 4°C. using dextran cross-linked with epichlorohydrin (commercially available under the trade name "Sephadex A 150"). A 0.005 molar tris-HCl buffer solution (pH 7.0) containing 0.005 mol of EDTA per liter of buffer and 0.1 percent of sodium azide was used for elution.

After elution, the active fractions, i.e. those which crosslink fibrin in the test described above, were collected and the fibrin-stabilizing factor was precipitated therefrom at a temperature of 4°C. by the addition of about 25 g of ammonium sulfate per 100 ml of eluate.

This precipitate was isolated and dissolved in 0.005 molar tris-EDTA buffer of pH 7.0.

After dialyzing for 20 hours at a temperature of 4°C. against a 0.005 molar tris-EDTA buffer at pH 7.0, the fibrin-stabilizing factor was precipitated from the remaining solution by adjusting the pH to 5.0 with 2% acetic acid.

For the preparation of a dosage unit form, the residue obtained by centrifuging was dissolved in 200 ml of physiological sodium chloride solution containing 0.01 mol of EDTA per liter of solution. The pH of the solution was then adjusted to 7.0 using 0.2 M sodium hydroxide solution.

After addition of 10 ml of 20 percent human albumin, the solution was filtered under sterile conditions through an aseptic filter and dialyzed for 20 hours at 4°C. successively against a physiological sodium chloride solution and a physiological sodium chloride solution containing 0.5 percent of glucose.

The fibrin-stabilizing activity of the solution was determined in comparison with human plasma and the solution was diluted with sodium chloride solution containing glucose to an extent that the activity of 4 ml of solution corresponded to the activity of 250 – 300 ml of mixed plasma.

10 ml of 20 percent human albumin were also added per 250 ml of the diluted solution. After filtration under sterile conditions, the filtrate was drawn off in portions of 4 ml each and lyophilized.

The total amount of fibrin-stabilizing active substance obtained from 1500 kg of placentae provided 2000 packages each having a factor XIII activity corresponding to 250 ml of human mixed plasma. For isolating the same amount of fibrin cross-linking active substance from plasma, about 4000 – 6000 liters of blood would be required, corresponding to about 8000 – 12000 blood donations each of 500 ml.

What is claimed is:

1. A process for isolating a fibrin-stabilizing factor which comprises:
   a. extracting human placentae at a temperature from 0°C. to 20°C. with a dilute aqueous sodium chloride solution and removing solid contaminants from the extract;
   b. adding a dilute aqueous solution of diaminoethoxy-acridine lactate to said extract at a temperature from 5°C. to 20°C. and at a pH between 5.0 and 7.5 in an amount furnishing 6 to 10 grams of said lactate per 100 grams of protein content in said extract to form a first precipitate, and isolating said first precipitate;
   c. dissolving said precipitate at a temperature from 5°C. to 20°C. in a dilute solution of alkali metal chloride at a pH between 7.0 and 8.0, said solution containing about 5 percent, by weight of said alkali metal chloride, of a complexing agent selected from the group consisting of ethylene diamine tetraacetic acid and nitrilo-triacetic acid, and removing any insoluble substances from the solution;
   d. adding a quaternary ammonium base to the solution in an amount from 0.04 to 0.08 percent, by weight of the solution, at a temperature from 5°C. to 20°C. to form a second precipitate, and removing and discarding this second precipitate;
   e. adding a dilute aqueous solution of diaminoethoxy-acridine lactate to the solution at a temperature from 5°C. to 20°C. to form a third precipitate, and isolating said third precipitate;
   f. dissolving said third precipitate in a dilute solution of an alkali metal chloride at a temperature from 5°C. to 20°C. and at a pH between 7.0 and 8.0, said solution containing about 5 percent, by weight of said alkali metal chloride, of ethylene diamine tetraacetic acid or nitrilo-triacetic acid and removing any insoluble substances from the solution;
   g. adding 20 to 30 percent of solid ammonium sulfate to the solution to form a fourth precipitate, and isolating said fourth precipitate;

h. forming a paste from said fourth precipitate and a dilute solution of ethylene diamine tetraacetic acid or nitrilo-triacetic acid and dialyzing said paste against tris(hydroxymethyl)-aminoethane/hydrochloric acid buffer containing ethylene diamine tetraacetic acid or nitrilo-triacetic acid and sodium azide, whereby the paste is solubilized;

i. adjusting the pH of the dialyzed solution to 6.0 to form a fifth precipitate which is separated and discarded, and readjusting the pH to 7.0;

j. gel filtering the solution on cross-linked dextran, eluting with tris(hydroxymethyl)-aminomethane/-hydrochloric acid buffer containing ethylene diamine tetraacetic acid or nitrilo-triacetic acid and sodium azide, and collecting and combining active fractions having an activity of more than 2 units of fibrin-stabilizing factor;

k. adding sufficient solid ammonium sulfate to the collected active fractions to form a sixth precipitate containing the fibrin-stabilizing factor, and isolating said sixth precipitate;

l. dissolving said sixth precipitate in a neutral tris(hydroxymethyl)-aminomethane/ethylene diamine tetraacetic acid buffer;

m. dialyzing the solution against neutral tris(hydroxymethyl)-aminomethane/ethylene diamine tetraacetic acid buffer;

n. adjusting the pH of the dialyzed solution to 5.0 to precipitate the fibrin-stabilizing factor and isolating the precipitate.

* * * * *